United States Patent
Gu et al.

(10) Patent No.: US 8,709,819 B2
(45) Date of Patent: Apr. 29, 2014

(54) PREPARATION AND ITS USE OF DERIVATIZATION REAGENT FOR DETECTING L-CARNITINE OR D-CARNITINE

(76) Inventors: Shuhua Gu, Jiangshu (CN); Qingyi Li, Jiangshu (CN); Xuecheng Wang, Jiangshu (CN)

( * ) Notice: Subject to any disclaimer, the term of this patent is extended or adjusted under 35 U.S.C. 154(b) by 406 days.

(21) Appl. No.: 13/121,388

(22) PCT Filed: Oct. 9, 2009

(86) PCT No.: PCT/CN2009/001127
§ 371 (c)(1),
(2), (4) Date: Aug. 4, 2011

(87) PCT Pub. No.: WO2010/043112
PCT Pub. Date: Apr. 22, 2010

(65) Prior Publication Data
US 2011/0281293 A1 Nov. 17, 2011

(30) Foreign Application Priority Data
Oct. 13, 2008 (CN) .......................... 2008 1 0195330

(51) Int. Cl.
*G01N 30/02* (2006.01)
(52) U.S. Cl.
USPC .......................................... 436/89; 436/111

(58) Field of Classification Search
USPC .................................................... 436/111, 89
See application file for complete search history.

(56) References Cited

FOREIGN PATENT DOCUMENTS

CN 1301240 * 2/2007

OTHER PUBLICATIONS

Spahn, Arch. Pharm. (Weinheim), 321, 847-850, 1998.*
Christopher J. McEntyre et al.: 'A high performance liquid chromatographic method for the measurement of total carnitine in human plasma and urine' Clinica Chimica Acta vol. 344, 2004, pp. 123-130.*

* cited by examiner

*Primary Examiner* — Monique Cole
(74) *Attorney, Agent, or Firm* — Squire Sanders (US) LLP

(57) ABSTRACT

A preparation method and its use of derivatization reagent for detecting L-carnitine or D-carnitine are provided. The present reagent is stable. It can be used for detecting L-carnitine or D-carnitine accurately and sensitively. That is to say, the reagent is applied to detecting the amount of synthesized or natural L-carnitine and the amount of mixing D-carnitine. The compound reagent is used for determining the chiral isomers of chemicals, biological reagents, health care reagents, cosmetic, body fluids and various foods, which contain L-carnitine or/and D-carnitine, and optical isomers of other chiral amino acids.

14 Claims, 2 Drawing Sheets

PREPARATION AND ITS USE OF DERIVATIZATION REAGENT FOR DETECTING L-CARNITINE OR D-CARNITINE

FIELD OF THE INVENTION

This invention relates to preparation and its use of derivatization reagent for detecting L-carnitine or D-carnitine.

BACKGROUND OF THE INVENTION

L-carnitine has a variety of physiological functions, which the basic one is to "transport" long-chain fatty acids into mitochondria via mitochondrial membrane where the β oxidation happens. L-carnitine is essential to fatty acid metabolism that once the synthesis of carnitine is blocked in body, or carnitine is degraded or excreted excessively, or the function of carnitine transferase decreases or losses, disturbance of lipid metabolism occurs which affects energy supply and leads to many diseases. Typical extraction method for natural L-carnitine is extracting from beef which is reported by Cater in 1952. However because the absolute content of L-carnitine is very low in meat, and the choline existing in gravy which is very similar in structure makes it is difficult to separate them, the direct extracting method is complicated, with low yield and high price. Therefore, it is not easy to get abundant natural L-carnitine.

Currently, L-carnitine for medicinal use is usually synthesized artificially. Usually, separation of racemic compounds is used for L-carnitine synthesis. The raw materials are cheap and easy to get, the process is easy to industrialize. However, because the defects of traditional chemical resolution, D-isomer can not be removed completely, the synthetic L-carnitine is not absolutely laevorotatory, but contains D-carnitine.

Natural carnitine is L-carnitine, and only L-carnitine is physiological active is a competitive inhibitior of carnitine acetyl transferase (CAT) and carnitine palmityl transferase (PTC). Therefore about 10% patients suffered myasthenia gravis after taking the DL-carnitine (Martindale: the Extra Pharmacopoeia (33th): 1356). Therefore taking drug safety into consideration, it's necessary to strictly control the content of the D-carnitine in the chemical synthetic process.

Currently, the content of D-Carnitine is detected by specific rotation which is lack of accuracy. In order to detect accurately the content of D-carnitine in L-carnitine products, and provide much safer and more effective drugs, health products and food, it is necessary to develop a method to detect the content of D-carnitine in L-carnitine products which is more accurate and sensitive.

SUMMARY OF THE INVENTION

One object of this invention is to provide a reagent for detecting the content of L-carnitine (or D-carnitine) and its preparation. The preparation method disclosed in the present invention is simple, economical. The reagent produced by this method is stable during preservation and is easy to use.

The second object of this invention is to provide a method to detect the content of L-carnitine (or D-carnitine) in active pharmaceutical ingredients of L-carnitine or D-carnitine, and in various pharmaceutical preparations or biological agents, health care products, cosmetics, body fluids and various food products which contain L-carnitine or/and D-carnitine. The detection method disclosed in the present invention has high sensitivity and is convenient and efficient.

The present invention discloses an optically pure derivatization reagent of formula (I) for detecting the content of L-carnitine (or D-carnitine):

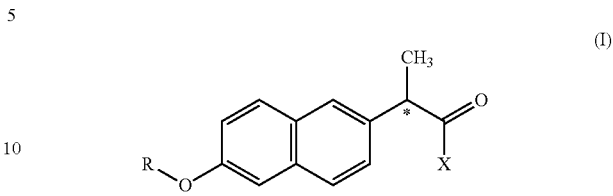

wherein, the carbon atom marked with an asterisk is the chiral carbon atom; the compounds in the present invention are chiral compounds having pure optical active, the D- or L-compound; R represents C1-C6 straight-chain or branched alkyl groups, C6-C10 aryl groups, C2-C6 straight-chain or branched alkenyl or alkynyl groups or C3-C6 cycloalkyl groups; and X represents a halogen atom.

The compound of formula (I) used in the present invention, wherein R represents methyl, ethyl, isopropyl, butyl or benzyl, and X represents Cl or Br.

Preferably, the present invention discloses (+)α-methyl-6-methoxy-2-naphthyl acetyl chloride as the derivatization reagent for detecting the content of L-carnitine or D-carnitine.

The derivatization reagents for detecting the content of L-carnitine or D-carnitine disclosed in the present invention, preferably, are crystalline solid of optically pure compound of formula (I), which is more stable, difficulty decomposed, and easy to preserve comparing to its solution.

The crystalline solid of optically pure compound of formula (I) in the present invention is recrystal with suitable solvent; the said solvent is selected from: ether, propyl ether, tetrahydrofuran, acetone, methyl ethyl ketone, acetonitrile, propionitrile, ethyl acetate, n-hexane, dichloromethane, chloroform, or the mixture of any two or more solvents above.

The solvent for recrystallisation of optically pure compound of formula (I) is preferably acetonitrile.

The present invention also discloses using the optically pure compound of formula (I) as a derivatization reagent, which the preparation is dissolving the optically pure compound of formula (I) and its crystalline in solvents to form solutions with certain concentration, said solvent is selected from: ether, propyl ether, tetrahydrofuran, acetone, methyl ethyl ketone, acetonitrile, propionitrile, ethyl acetate, n-hexane, dichloromethane, chloroform, or the mixture of any two or more solvents above. The concentration of the solution is 0.01~100 mg/ml. Specially preferably, the solvent is acetonitrile and the concentration of the solution is 1-10 mg/ml.

The crude active ingredient of formula (I) is produced by the steps below:

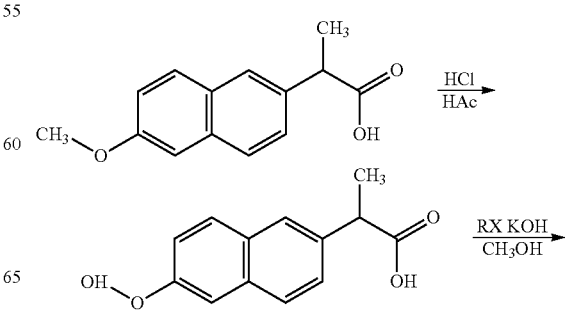

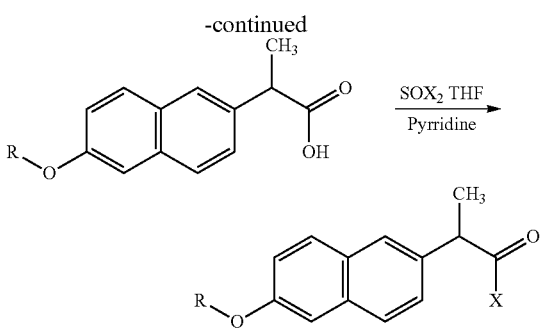

(+) or (−)α-methyl-6-methoxy-2-naphthyl acetic acid is hydrolyzed, and then the phenolichydroxyl group is combined with halohydrocarbon, the product forms crude acylhalide by acylation.

The present invention also discloses preparation of the crystalline solid of optically pure compound of formula (I) that the crude acylhalide is recrystallised with suitable solvent to form the crystalline solid. The said solvent is selected from ether, propyl ether, tetrahydrofuran, acetone, methyl ethyl ketone, acetonitrile, propionitrile, ethyl acetate, n-hexane, dichloromethane, chloroform, or the mixture of any two or more solvents above.

The solvent for recrystallisation of optically pure compound of formula (I) is preferably acetonitrile, so that the crystalline solid obtained has high optical purity, and can be stably preserved.

The present invention discloses the crystalline of optically pure compound of formula (I), (+)α-methyl-6-methoxy-2-naphthyl acetyl chloride, which has the characteristic of white and needle crystalline, m.p 92.3~93.5° C.; X-Ray data: diffraction angle (2θ) is 6.579 (d=13.4231, $I/I_0$=54.4), 10979 (d=8.0522, $I/I_0$=34.1), 13.218 (d=6.6925, $I/I_0$=72.2), 13.499 (d=6.5539, $I/I_0$=45.8), 18.222 (d=4.8646, $I/I_0$=21.2), 18.780 (d=4.7211, $I/I_0$=100.0), 19.901 (d=4.4577, $I/I_0$=21.7), 21.619 (d=4.1072, $I/I_0$=26.2), 22.100 (d=4.0188, $I/I_0$=75.3), 27.139 (d=3.2830, $I/I_0$=19.0), 47.681 (d=1.9057, $I/I_0$=15.0); IR: 3414.5 $cm^{-1}$, 2983.2 $cm^{-1}$, 1786.2 $cm^{-1}$, 1605.0 $cm^{-1}$, 1390.6 $cm^{-1}$, 1270.4 $cm^{-1}$, 1183.1 $cm^{-1}$, 823.8 $cm^{-1}$, 701.6 $cm^{-1}$, 7412 $cm^{-1}$; $^1$HNMR (CD3COCD3, 500 MHz): 1.66 (m, 3H), 3.78 (s, 3H), 4.46 (m, 1H), 7.19 (m, 1H), 7.29 (m, 1H), 7.43 (m, 1H), 7.82 (m, 1H), 7.83 (s, 1H), 7.85 (s, 1H); elemental analysis: C %: 67.76 (theoretical value is 67.61), H %: 5.25 (5.27).

MS: the molecular weight is 248, 250, it is the isotopic peak of chlorine, m/z 185 is the base peak with the abundances of 100%, from which can be supposed as the fragment ion of formula

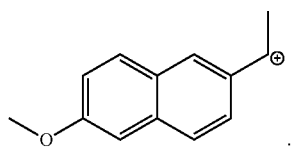

The present invention discloses a method for detecting the content of L-carnitine or D-carnitine in a sample; the detection includes the following steps:

(1) Prepare the test sample solution containing proper amount of L-carnitine (or D-carnitine) and the control solution containing DL-carnitine.

(2) Mix proper amount of derivative reagent of the present invention and the test sample solution containing L-carnitine (or D-carnitine), and let them react to afford L-carnitine (or D-carnitine) derivatives.

(3) Apply HPLC to detect and calculate the content of L-carnitine (or D-carnitine) in the sample.

The present invention discloses a method for detecting the content of L-carnitine or D-carnitine in a sample, wherein the detection includes the following steps:

(1) Prepare the derivatization reagent solution: D-type or L-type optical pure compound of formula (I) of any of claims 1 to 5 is dissolved in solvent to form a 0.01~100 mg/ml solution under the dark conditions, wherein the compound of formula (I) is preferably (+)α-methyl-6-methoxy-2-naphthyl acetyl chloride, and the solvent is preferably acetonitrile; the concentration of solution is preferably from 1 to 10 mg/ml.

(2) Prepare of the test solution of L-carnitine or D-carnitine, and control solution of DL-carnitine;

(3) Derived reagent of step (1) is mixed and reacted with test solution and control solution of step (2) respectively in a airtight vessel, in the present of solvent at 20° C.~95° C. in a water bath for 20 min to 180 min;

(4) HPLC is applied to separate and detect the reacted test solution and control solution, the content of L-carnitine (or D-carnitine) in test solution is calculated by external standard method.

Detailed detection also includes:

(1) Chromatographic conditions: The octadecyl silane bonded silica is taken as a filler, and triethylamine buffer (phosphate 8 ml, triethylamine, 15 ml, water 1500 ml)-tetrahydrofuran is taken as mobile phase for gradient elution. Excitation wavelength is from 230 nm to 260 nm and emission wavelength is from 340 nm to 380 nm.

(2) Preparation of test solution: test sample is precisely weighed and dissolved in water to form 0.1 μg/ml~3.0 μg/ml solution which is the test solution.

(3) Preparation of control solution: DL-carnitine is precisely weighed and desolved in water to form 0.2 μg/ml~6.0 μg/ml solution which is the control solution.

(4) Derivatization reaction: 30 μl of control solution and test solution is put in 5 ml volumetric flask respectively, for, each one, 0.01 mol/L~0.5 mol/L of carbonate buffer solution is added in, proper amount of pyridine acetonitrile solution (per 1 ml acetonitrile contains 1 μl~50 μl of pyridine) is mixed with derivatization reagent solution of the present invention, sealed and reacted at 20° C.~95° C. in warm water bath, which is diluted with acetic acid buffer to the scale, shaken and tilted right after removing from the bath.

(5) Content detection: the same amount of reacted test sample and the control solution is injected in HPLC respectively, chromatograms is recorded and the content of L-carnitine (or D-carnitine) in test solution is calculated by external standard method.

L-carnitine (or D-carnitine) content detection of the present invention, wherein the above mentioned chromatographic conditions of step (1) comprise a mobile phase which is a mix of the triethylamine buffer (phosphate 8 ml, triethylamine, 15 ml, water 1500 ml) and tetrahydrofuran. The pH value of triethylamine buffer solution is 2.0%~9.0. The gradient of the two components is 0-10 min, when the concentration of triethylamine buffer is 70%~90%, and that of THF is 30%~10%; it is 10%~11 min, when the concentration of triethylamine buffer is from 70% to 30%~90% to 30%, and that of THF is from 30% to 70%~10% to 70%; it is 11~18 min, when the concentration of triethylamine buffer is 30%, and that of tetrahydrofuran is 70%; it is 18~19 min, when the concentration of triethylamine buffer is from 30% to 70%~30% to 90%, and that of THF is from 70% to 30%~70% to 10%; it is 19~25 min, when the concentration of triethylamine buffer is 70%~90%, and that of THF is 30%~10%.

L-carnitine (or D-carnitine) content detection of the present invention, wherein control solution of step (3) is prepared in detail that DL-carnitine 2 mg~60 mg is weighted precisely and dissolved with water in a 100 mL of volumetric flask, volume, 10 ml of which is precisely pipetted into a 100 ml of volumetric flask, added water to volume. It is the control solution. When the concentration of L-carnitine (or D-carnitine) is 0.1 μg/ml~3.0 μg/ml, there is a good linear relationship, which the linear correlation coefficient r equals to 0.9991 and the recovery is 100.6%.

L-carnitine (or D-carnitine) content detection of the present invention, wherein derivatization reagent concentration of step (4) is 0.01~100 mg/ml, preferably is 1-10 mg/ml, most preferably is 5 mg/ml.

L-carnitine (or D-carnitine) content detection of the present invention, wherein carbonate buffer solution of step (4) prepared in detail that 4.2 g sodium bicarbonate is dissolved in 900 ml water, and pH value is adjusted with 5 mol/L of hydrogen sodium to 7.0~12.0, added water to 1000 mL.

L-carnitine (or D-carnitine) content detection of the present invention, wherein the quantity added in carbonate buffer solution of step (4) is 5 μl to 500 μl.

L-carnitine (or D-carnitine) content detection of the present invention, wherein the reaction temperature of step (4) is 20° C.-95° C., and reaction time is 20 min~180 min.

L-carnitine (or D-carnitine) content detection of the present invention, wherein the acetate buffer solution of step (4) is prepared in detail that 3.0 mL glacial acetic acid is dissolved with 900 mL water, and pH value is adjusted with 5 mol/L of sodium hydroxide solution to 2.0~7.0, and added water to 1000 mL.

The present invention discloses the derivatization reagent of the present invention and detection method, which is applied to detect the content of L-carnitine and/or D-carnitine in various pharmaceutical preparations or biological agents, health care products, cosmetics, body fluids and various food products which contain L-carnitine or/and D-carnitine, such as: L-carnitine API, injection, oral liquid, tablets, slimming capsules, drinks and etc.

The present invention discloses the derivatization reagent of the present invention and detection method, which is applied to detect the content of carnitine in the tissue and plasma of various mammals, including human.

The present invention discloses the derivatization reagent of the present invention and detection method, which is applied to detect the content of carnitine in various edible plant and animal food. Such as: pig, cattle, sheep, chicken, shrimp, fish, eggs, vegetables, fruits and etc.

The present invention discloses the derivatization reagent of the present invention and detection method, which is applied to detect the content of carnitine in various animal feed.

The present invention discloses the derivatization reagent of the present invention and detection method, which is applied to detect the content of carnitine in various plant nutrients.

The present invention discloses the derivatization reagent of the present invention and detection method, which is applied to detect the optical purity other chiral amino acids.

The description of the code used in the invention:

D-: D-isomer
L-: L-isomer
IR: infrared absorption spectroscopy
HNMR: H Nuclear Magnetic Resonance
MS: mass spectrometry
HPLC: high performance liquid chromatography
(+) MNPC: (+)α-methyl-6-methoxy-2-naphthyl acetyl chloride
(+) ENPC: (+)α-methyl-6-ethoxy-2-naphthyl acetyl chloride
(+) PNPC: (+)α-methyl-6-isopropoxy-2-naphthyl acetyl chloride
(+) BUNPC: (+)α-methyl-6-butoxy-2-naphthyl acetyl chloride
(+) BNPC: (+)α-methyl-6-benzoxy-2-naphthyl acetyl chloride

DETAILED DESCRIPTION OF THE INVENTION

Figure 1:
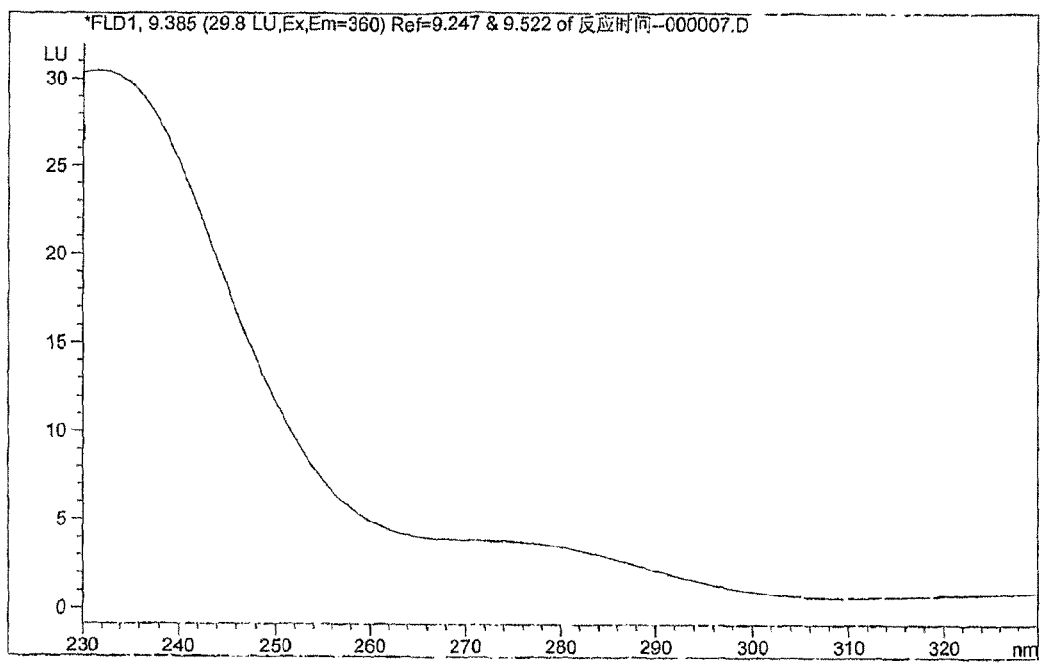
FIG. 1 is the excitation spectrum of detecting the content of L-carnitine (or D-carnitine)
Figure 2:
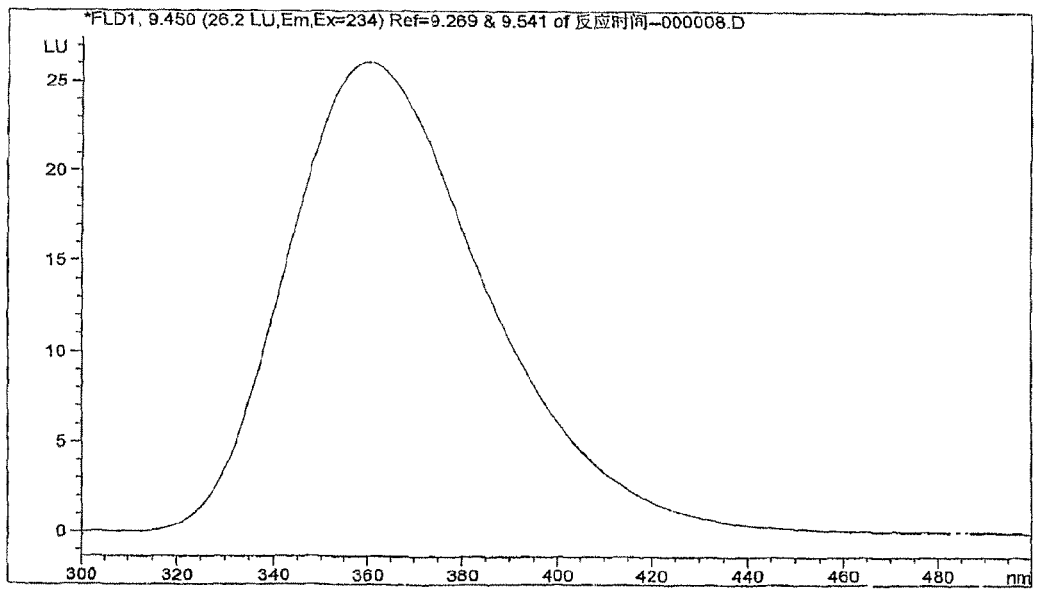
FIG. 2 is the emission spectrum of detecting the content of L-carnitine (or D-carnitine)
Figure 3:
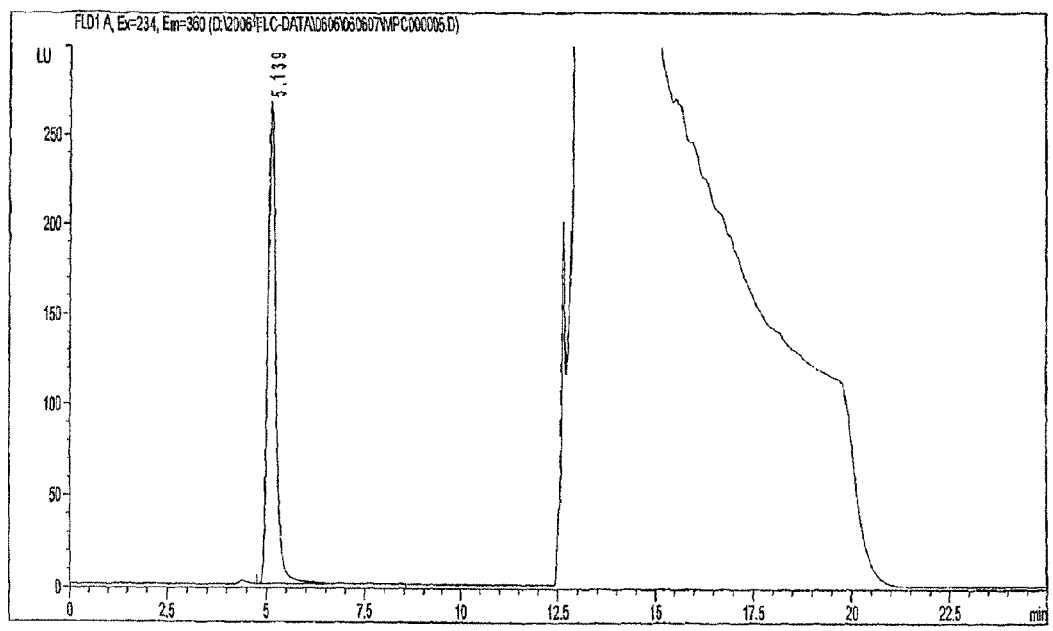
FIG. 3 is the HPLC of detecting the content of L-carnitine [L-carnitine (tR=5.139 min)]
Figure 4:
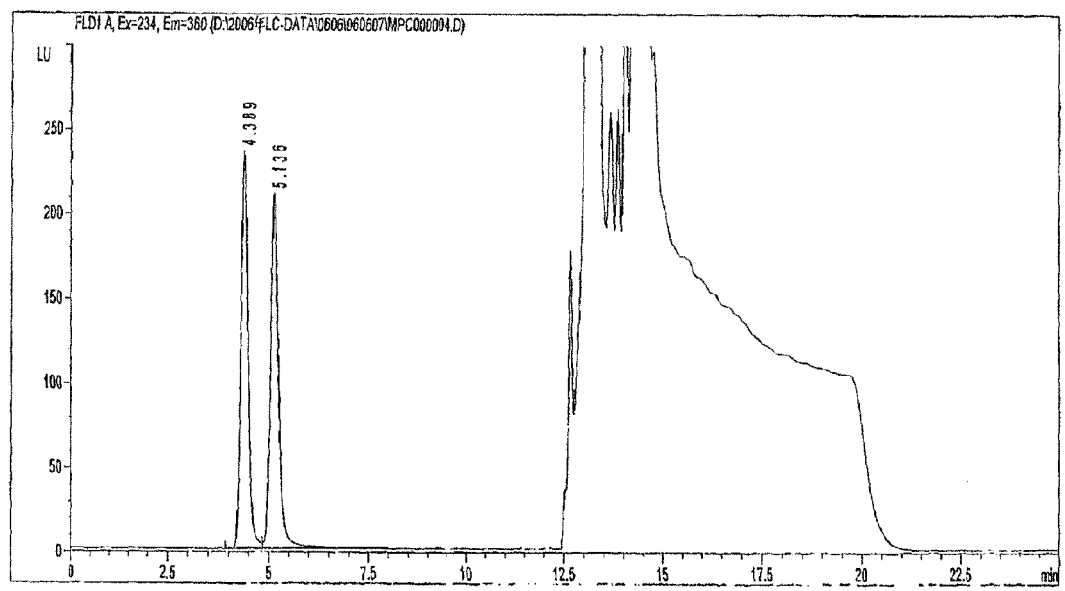
FIG. 4 is the HPLC of detecting the content of L-carnitine [D-carnitine (tR=4.389 min), L-carnitine (tR=5.136 min)].

The following implementations are used to explain the present invention, but not limit the scope of this invention.

Example 1

Preparation of (+)α-methyl-6-methoxy-2-naphthyl acetyl chloride ((+) MNPC)

4.6 g (+)α-methyl-6-methoxy-2-naphthyl acetic acid and 50 ml THF was added in a 100 ml of single neck bottle, cooled with ice water, stirred with magnetic force, added 2 ml SOCl2, added proper amount of pyridine, reacted for 6 h, dried by rotary, added 20 ml acetonitrile, cooled to give faint yellow solid, recrystallised with 15 ml acetonitrile to give white needle crystal. Dried under vacuum to give 2.87 g of product, yield 57%, m.p 92.3-93.5° C.

IR: 3414.5 $cm^{-1}$, 2983.2 $cm^{-1}$, 1786.2 $cm^{-1}$, 1605.0 $cm^{-1}$, 1390.6 $cm^{-1}$, 1270.4 $cm^{-1}$, 1183.1 $cm^{-1}$, 832.8 $cm^{-1}$, 701.6 $cm^{-1}$, 472.2 $cm^{-1}$.

1HNMR ((CD3COCD3, 500 MHz): 1.66 (m, 3H), 3.78 (s, 3H), 4.46 (m, 1H), 7.19 (m, 1H), 7.29 (m, 1H), 7.43 (m, 1H), 7.82 (m, 1H), 7.83 (s, 1H), 7.85 (s, 1H);

X-Ray data: diffraction angle (2θ) is 6.579 (d=13.4231, $I/I_0$=54.4), 10979 (d=8.0522, $I/I_0$=34.1), 13.218 (d=6.6925, $I/I_0$=72.2), 13.499 (d=6.5539, $I/I_0$=45.8), 18.222 (d=4.8646, $I/I_0$=21.2), 18.780 (d=4.7211, $I/I_0$=100.0), 19.901 (d=4.4577, $I/I_0$=21.7), 21.619 (d=4.1072, $I/I_0$=26.2), 22.100 (d=4.0188, $I/I_0$=75.3), 27.139 (d=3.2830, $I/I_0$=19.0), 47.681 (d=1.9057, $I/I_0$=15.0);

MS: MW 248, 250, it is the isotopic peak of chlorine, m/z 185 is the base peak with the abundances of 100%, from which can be supposed as the fragment ion of formula

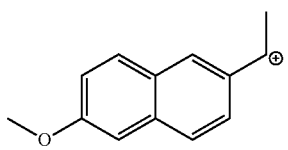

Elemental analysis: C %: 67.76 (theoretical value is 67.61), H %: 5.25 (5.27)

Example 2

Preparation of (+)α-methyl-6-ethoxy-2-naphthyl acetyl chloride ((+) ENPC)

Step 1

50 g (+)α-methyl-6-ethoxy-2-naphthyl acetic acid was dissolved in 205 ml glacial acetic acid, heated under reflux, added 20 ml of 36% HCl in each 30 min, reacted for 6 h. and poured into 600 g ice water, filtered, recrystallised with ethanol-water, dried to give colorless crystal (9.87 g), yield 90.5%, m.p 189.4~191.3° C.;

IR: 3411.1 cm$^{-1}$, 1701.4 cm$^{-1}$, 1632.5 cm$^{-1}$, 1606.2 cm$^{-1}$, 1509.1 cm$^{-1}$, 1384.4 cm$^{-1}$, 1189.0 cm$^{-1}$, 1147.3 cm$^{-1}$, 865.9 cm$^{-1}$, 477.8 cm$^{-1}$.

1HNMR ((CD3COCD3, 500 MHz): δ1.53 (m, 3H), 3.98 (s, 3H), 7.15 (m, 1H), 7.20 (m, 1H), 7.42 (m, 1H), 7.67 (m, 1H), 7.73 (s, 1H), 7.76 (m, 1H), 8.55 (s, 1H);

Step 2

The product of step 1 (41.0 g) and KOH (32.0 g) was dissolved in 200 ml of methanol, added 35.5 ml bromoethane, heated under reflux for 2 h, added 200 ml of 5% NaOH after cooled, and reacted for 3~4 h, added 600 ml ice water after reaction, stirred, rested and filtered, washed with water, recrystallised with 500 ml ethanol and dried at 80° C. to give product (37.2 g), yield 80.3%, m.p 151.8~155.6;

IR: 3453.5 cm$^{-1}$, 1729.6 cm$^{-1}$, 1609.5 cm$^{-1}$, 1604.5 cm$^{-1}$, 1393.7 cm$^{-1}$, 1181.9 cm$^{-1}$, 1158.4 cm$^{-1}$, 862.4 cm$^{-1}$, 481.8 cm$^{-1}$.

1HNMR ((CD3COCD3, 500 MHz): σ1.43 (m, 3H), 1.53 (m, 3H), 3.90 (m, 1H), 4.16 (m, 2H), 7.15 (m, 1H), 7.25 (m, 1H), 7.46 (m, 1H), 7.75 (s, 1H), 7.76 (s, 1H), 7.79 (s, 1H).

Step 3

Formation of acyl chloride from the product of step 2 according to example 1, m.p 91.7~92.9° C.

IR: 3416.7 cm$^{-1}$, 2982.1 cm$^{-1}$, 1785.9 cm$^{-1}$, 1605.2 cm$^{-1}$, 1309.5 cm$^{-1}$, 1269.1 cm$^{-1}$, 1182.6 cm$^{-1}$, 832.8 cm$^{-1}$, 701.8 cm$^{-1}$, 472.6 cm$^{-1}$.

1HNMR ((CD3COCD3, 500 MHz): σ1.43 (m, 3H), 1.66 (m, 3H), 4.18 (m, 2H), 4.46 (m, 1H), 7.19 (m, 1H), 7.29 (m, 1H), 7.43 (m, 1H), 7.82 (m, 1H), 7.83 (s, 1H), 7.85 (s, 1H)

Example 3

Preparation of (+)α-methyl-6-isopropoxy-2-naphthyl acetyl chloride ((+) PNPC)

2-bromopropane was used in step 2 according to the method of example 1 to give (+) PNPC, m.p 77.8~79.4° C.;

IR: 3416.3 cm$^{-1}$, 1784.5 cm$^{-1}$, 1604.8 cm$^{-1}$, 1390.2 cm$^{-1}$, 1270.3 cm$^{-1}$, 1182.5 cm$^{-1}$, 854.6 cm$^{-1}$, 699.2 cm$^{-1}$, 469.5 cm$^{-1}$.

1HNMR ((CD3COCD3, 500 MHz): δ 1.06 (m, 3H), 1.65 (m, 3H), 1.83 (m, 2H), 4.07 (m, 2H), 4.45 (m, 1H), 7.19 (m, 1H), 7.29 (m, 1H), 7.42 (m, 1H), 7.81 (m, 1H), 7.82 (s, 1H), 7.84 (m, 1H).

Example 4

Preparation of (+)α-methyl-6-butoxy-2-naphthyl acetyl chloride ((+)BUNPC)

Bromobutane was used in step 2 according to the method of example 1 to give (+) BUNPC, m.p 56.3~57.3° C.;

IR: 3415.7 cm$^{-1}$, 1785.3 cm$^{-1}$, 1605.2 cm$^{-1}$, 1468.3 cm$^{-1}$, 1392.3 cm$^{-1}$, 1268.9 cm$^{-1}$, 1178.3 cm$^{-1}$, 921.8 cm$^{-1}$, 819.9 cm$^{-1}$, 727.45 cm$^{-1}$, 747.6 cm$^{-1}$.

1HNMR ((CD3COCD3, 500 MHz): δ1.00 (m, 3H), 1.55 (m, 2H), 1.67 (m, 3H), 1.82 (m, 2H), 4.14 (m, 2H), 4.48 (m, 2H), 7.19 (m, 1H), 7.31 (m, 1H), 7.42 (m, 1H), 7.82 (m, 1H), 7.83 (s, 1H), 7.85 (m, 1H).

Example 5

Preparation of (+)α-methyl-6-benzoxy-2-naphthyl acetyl chloride ((+) BNPC)

Benzyl bromide was used in step 2 according to the method of example 1 to give (+) BUNPC, m.p 77.2~79.1° C.

1HNMR ((CD3COCD3, 500 MHz): δ1.6 (d, 3H), 3.81 (m, 1H), 4.14 (m, 2H), 4.48 (m, H), 5.26 (s, 2H), 7.19 (m, 1H), 7.22 (m, 1H), 7.38 (m, 3H), 7.42 (m, 1H), 7.47 (m, 2H), 7.83 (m, 1H), 7.87 (m, 1H), 7.90 (m, 1H).

Example 6

Derivatization reaction and chromatographic conditions

1. Chromatographic Conditions and Systematic Adaptability Test:

Agilent 1100 HPLC; fluorescence detector; column: C18-ODS column (4.6×150 mm, 5 μm); the total flow rate: 1 ml/min; mobile phase: the triethylamine buffer (phosphate 8 ml, triethylene amine 15 ml, water 1500 ml, pH adjusted to 5.4)-tetrahydrofuran mixture, the time gradient of the following Table 1:

TABLE 1

| HPLC time gradient table | | |
|---|---|---|
| Time (min) | Triethylamine buffer (%) | THF (%) |
| 0 | 75 | 25 |
| 10 | 75 | 25 |
| 11 | 30 | 70 |
| 18 | 30 | 70 |
| 19 | 75 | 25 |
| 25 | 75 | 25 |

Number of theoretical plates was greater than 5000, and the resolution of the peak both of L-carnitine and D-carnitine was more than 1.5.

2. Detection Wavelength

The spectral scan was carried out after derivatization reaction (FIG. 1, 2). Ultimately the excitation wavelength of 234 nm and emission wavelength of 360 nm was chosen.

3. Preparation of Control Solution 20 mg DL-carnitine was precisely wighted and dissolved with water in 100 mL volumetric flask to volume, and then 10 ml solution was precisely pipetted in 100 ml volumetric flask, added water to volume. It is the control solution.

4. Derivatization Reaction:

30 μl of control solution and test solution is put in 5 ml volumetric flask respectively, for, each one, 100 μl of 0.05 mol/L carbonate buffer solution (4.2 g sodium bicarbonate was dissolved in 900 ml water, pH was adjusted to 8.4 with 5 mol/L NaOH), 100 μl of pyridine acetonitrile solution (per 1 ml acetonitrile contains 25 μl of pyridine) and 200 μl of derivatization reagent solution (0.5% (+)α-methyl-6-methoxy-2-naphthyl acetyl chloride) is mixed, sealed and reacted at 40° C. in worm water bath for 60 min, which is diluted with acetic acid buffer (3 ml glacial acetic acid was dissolved in 900 ml water, pH was adjusted with 5 mol/L NaOH to 7.0, added water to 1000 mL) to the scale, shaken and felted right after remove from the bath.

5. Detection: 10 μl of reacted test sample and the control solution is injected in HPLC respectively, chromatograms is recorded and the content of L-carnitine (or D-carnitine) in test solution is calculated by external standard method When sample concentration of L-carnitine (or D-carnitine) is 0.33 μg/ml~1.64 μg/ml, there was a good linear relationship, and linear correlation coefficient r equaled to 0.9991, and recovery was 100.6%.

Example 7

Crystallization of the Compound of Formula (I) and the Stability of the Solution Containing the Compound An accurate content of derivatization reagent is the ensurance of accurate results. However, the compounds of formula (I) are acyl chloride which is active chemically and easily decomposed in water, it is necessary to find a proper preservation and use conditions which include choosing suitable solvent to ensure the stability of the compounds of formula (I) and decreases the detecting error The solvent is selected from ether, propyl ether, tetrahydrofuran, acetone, methyl ethyl ketone, acetonitrile, propionitrile, ethyl acetate, and etc, the crystal, is dissolved in solvent to form solution, the stability of crystal and solution is detected together.

The stability tests of 5 mg/ml of (+)α-methyl-6-methoxy-2-naphthyl chloride ((+) MNPC) solutions (dissolved in acetonitrile, acetone, ethyl acetate respectively) and relative solid crystal were carried on the experimental data was shown in table 2, table 3, table 4, and table 5.

TABLE 2

Investigation of (+)MNPC solid's stability

| | Refrigerated storage time (months) | | | | | |
| --- | --- | --- | --- | --- | --- | --- |
| | Fresh | 0.5 | 1 | 2 | 3 | 6 | 12 |
| (+) MNPC content (%) | 99.55 | 99.50 | 99.53 | 99.39 | 99.30 | 99.09 | 98.52 |
| (−) MNPC content (%) | 0.12 | 0.13 | 0.12 | 0.13 | 0.14 | 0.15 | 0.15 |
| Other impurities (%) | 0.33 | 0.37 | 0.35 | 0.48 | 0.56 | 0.76 | 1.33 |

Note:
storage condition, dispensed in brown glass, sealed and freeze-preserved (−15° C.) -

TABLE 3

Investigation of (+)MNPC acetonitrile solution's stability

| | Refrigerated storage time (day) | | | | | |
| --- | --- | --- | --- | --- | --- | --- |
| | Fresh | 3 | 10 | 20 | 30 | 50 | 80 |
| (+) MNPC content (%) | 99.55 | 99.55 | 99.51 | 99.09 | 99.55 | 99.15 | 97.48 |
| (−) MNPC content (%) | 0.12 | 0.13 | 0.16 | 0.19 | 0.16 | 0.23 | 0.31 |
| Other impurities (%) | 0.33 | 0.32 | 0.33 | 0.72 | 0.29 | 0.62 | 2.21 |

Note:
storage condition, dispensed in brown glass, sealed and freeze-preserved (−15° C.)

TABLE 4

Investigation of (+)MNPC acetone solution's stability

| | Refrigerated storage time (day) | | | | | |
| --- | --- | --- | --- | --- | --- | --- |
| | Fresh | 3 | 10 | 20 | 30 | 50 | 80 |
| (+) MNPC content (%) | 99.55 | 99.04 | 98.64 | 97.33 | 96.21 | 94.83 | 90.51 |
| (−) MNPC content (%) | 0.12 | 0.15 | 0.17 | 0.21 | 0.24 | 0.42 | 0.73 |
| Other impurities (%) | 0.33 | 0.81 | 1.19 | 2.46 | 3.55 | 4.75 | 8.76 |

Note:
storage condition, dispensed in brown glass, sealed and freeze-preserved (−15° C.)

TABLE 5

Investigation of (+) MNPC ethyl acetate solution's stability

| | Refrigerated storage time (day) | | | | | |
| --- | --- | --- | --- | --- | --- | --- |
| | Fresh | 3 | 10 | 20 | 30 | 50 | 80 |
| (+) MNPC content (%) | 99.55 | 95.88 | 90.90 | 84.13 | 67.96 | 50.22 | 16.52 |
| (−) MNPC content (%) | 0.12 | 0.98 | 1.77 | 3.11 | 3.85 | 4.01 | 4.82 |
| Other impurities (%) | 0.33 | 3.14 | 7.33 | 12.76 | 28.19 | 45.77 | 78.66 |

Note:
storage condition, dispensed in brown glass, sealed and freeze-preserved (−15° C.)

It is shown in from table 2 to table 5 that solid crystal of MNPC is more stable than any solution in all samples, and in all the solutions the MNPC acetonitrile solution had the best stability which the content decreased obviously since the 60th day while others were even worse. Therefore, MNPC solid crystal has the best stability, as a derivatization reagent, it is suitable for long-term preservation and transportation; in all the solutions, the MNPC acetonitrile solution has the best stability, acetonitrile is a suitable solvent for preparing the derivatization reagent and conducting derivatives reaction.

Example 8

Precise detection of the content of D-Carnitine in synthetic L-carnitine 100 mg L-carnitine was precisely weighted and dissolved with water in 100 ml of volumetric flask to volume, 10 ml solution was pipetted in 100 ml volumetric flask, added water to volume, which is the sample solution; 20 mg DL-carnitine was weighted and dissolved with water in 100 ml volumetric flask to volume, and 1 ml solution was pipetted in 100 ml volumetric flask, added water to volume, which is the control solution.

30 μl of control solution and sample solution was pipetted precisely respectively in 5 ml volumetric flask, for each one, 100 μl of 0.05 mol/L carbonate buffer solution (4.2 g sodium bicarbonate was dissolved in 900 ml water, pH was adjusted to 8.4 with 5 mol/L NaOH), 100 μl of pyridine acetonitrile solution (per 1 ml acetonitrile contains 25 μl of pyridine) and 200 μl of derivatization reagent solution (0.5% (+)α-methyl-6-methoxy-2-naphthyl acetyl chloride) was mixed, sealed and reacted at 40° C. in worm water bath for 60 min, which was diluted with acetic acid buffer (3 ml glacial acetic acid was dissolved in 900 ml water, pH was adjusted with 5 mol/L NaOH to 7.0, added water to 1000 mL) to the scale, shaken and lilted right after remove from the bath. 10 μl of control solution and sample solution was pipetted and injected respectively in HPLC, chromatograph was recorded and the content of D-carnintine was calculated by external standard method The result was shown in table 6.

TABLE 6

Detection of D-carnitine in synthetic L-carnitine

| | 1 | 2 | 3 | 4 | 5 | 6 | Average | RSD |
|---|---|---|---|---|---|---|---|---|
| D-carnitine (%) | 0.99 | 0.97 | 1.00 | 0.98 | 1.00 | 0.98 | 0.99 | 1.22% |

Example 9

Detection of the Content of L-Carnitine 10 mg L-carnitine was precisely weighted and dissolved with water in 100 ml of volumetric flask to volume, 1 ml solution was pipetted in 100 ml volumetric flask, added water to volume, which is the sample solution; 20 mg DL-carnitine was weighted and dissolved with water in 100 ml volumetric flask to volume, and 1 ml solution was pipetted in 100 ml volumetric flask, added water to volume, which is the control solution.

30 μl of control solution and sample solution was pipetted precisely respectively in 5 ml volumetric flask, for each one, 100 μl of 0.05 mol/L carbonate buffer solution (pH=8.4), 100 μl of pyridine acetonitrile solution and 100 μl of 0.5% derivatization reagent acetonitrile solution was mixed, sealed and reacted at 40° C. in worm water bath for 60 min, which was diluted with 0.05 mol/L acetic acid buffer (pH 7.0) to the scale, shaken and tilted right after remove from the bath. 10 μl of control solution and sample solution was pipetted and injected respectively in HPLC, chromatograph was recorded and the content of D-carnintine was calculated by external standard method The result was shown in table 8.

TABLE 8

Detection of L-carnitine

| | 1 | 2 | 3 | 4 | 5 | 6 | Average | RSD |
|---|---|---|---|---|---|---|---|---|
| L-carnitine (%) | 98.53 | 98.88 | 98.82 | 98.67 | 99.13 | 98.72 | 98.79 | 0.21% |

Example 10

Detection of L-Carnitine and D-Carnitine in L-Carnitine API Synchronously 100 mg food containing L-carnitine was weight precisely and dissolved in 100 ml of volumetric flask to volume, 1 ml solution was pipetted in 100 ml volumetric flask, added water to volume, which is the sample solution; 20 mg DL-carnitine was weighted and dissolved with water in 100 ml volumetric flask to volume, which was the control 1; and 1 ml "control 1" solution was pipetted in 100 ml volumetric flask, added water to volume, which is the control 2.

30 μl of "control 1", "control 2" and sample solution was pipetted precisely respectively in 5 ml volumetric flask, for each one, 100 μl of 0.05 mol/L carbonate buffer solution (4.2 g sodium bicarbonate was dissolved in 900 ml water, pH was adjusted to 8.4 with 5 mol/L NaOH), 100 μl of pyridine acetonitrile solution (per 1 ml acetonitrile contains 25 μl of pyridine) and 100 μl of derivatization reagent solution (0.5% (+)α-methyl-6-methoxy-2-naphthyl acetyl chloride) was mixed, sealed and reacted at 40° C. in worm water bath for 60 min, which was diluted with acetic acid buffer (3 ml glacial acetic acid was dissolved in 900 ml water, pH was adjusted with 5 mol/L NaOH to 7.0, added water to 1000 mL) to the scale, shaken and filted right after remove from the bath. 10 μl of control solution and sample solution was pipetted and injected respectively in HPLC, chromatograph was recorded and the content of D-carnintine was calculated by external standard method. The result was shown in table 9.

TABLE 9

Detection for L-carnitine API

| | 1 | 2 | 3 | 4 | 5 | 6 | Average | RSD |
|---|---|---|---|---|---|---|---|---|
| L-carnitine (%) | 98.01 | 97.75 | 98.57 | 97.83 | 98.19 | 97.64 | 98.00 | 0.35% |
| D-carnitine (%) | 0.58 | 0.61 | 0.59 | 0.59 | 0.61 | 0.60 | 0.60 | 2.03% |

Example 11

Detection of the Content of L-Carnitine in Injection

L-carnitine injection (5 ml: 1 g) 1 mL was pipetted precisely in 100 mL volumetric flask, added water to volume, 1 ml of the solution was pipetted precisely in 100 ml volumetric flask, added water to volume, and 5 ml of the solution was pipetted precisely in 100 ml, added water to volume. It is the sample solution.

The method of example 9 was used for detection and the result was shown in table 10.

TABLE 10

Detection of L-carnitine injection (labelled amount)

| | 1 | 2 | 3 | 4 | 5 | 6 | Average | RSD |
|---|---|---|---|---|---|---|---|---|
| L-carnitine (%) | 100.55 | 99.81 | 100.19 | 99.72 | 100.3 | 100.39 | 100.16 | 0.33% |

Example 12

Detection of the Content of L-Carnitine in Oral Solution

L-carnitine oral solution (10 ml: 1 g) 1 mL was pipetted precisely in 100 ml volumetric flask, added water to volume, 1 ml of the solution was pipetted precisely in 100 ml volumetric flask, added water to volume, and 10 ml of the solution was pipetted precisely in 100 ml, added water to volume. It is the sample solution.

The method of example 9 was used for detection and the result was shown in table 11.

TABLE 11

Detection for L-carnitine oral solution (labeled amount)

| | 1 | 2 | 3 | 4 | 5 | 6 | Average | RSD |
|---|---|---|---|---|---|---|---|---|
| L-carnitine (%) | 97.88 | 98.05 | 97.55 | 98.23 | 97.77 | 97.71 | 97.86 | 0.25% |

Example 13

Detection of the Content of L-Carnitine in Slimming Capsule

20 L-carnitine slimming capsules were weighted precisely, the contents of capsules were poured out (without losing capsule shell which was weighted followed by cleaning with small brush); the contents of capsules were mixed, porphyrized, weighted properly (equaled to 10 mg L-carnitine) and put in 100 ml volumetric flask, added water and treated with ultrasound for 30 min, added water to volume after complete dissolving, fluted, and then pipetted 1 ml to 100 ml volumetric flask, added water to volume, it is sample solution.

The method of example 9 was used for detection and the result was shown in table 12.

TABLE 12

Detection for L-carnitine slimming capsule

| | 1 | 2 | 3 | 4 | 5 | 6 | Average | RSD |
|---|---|---|---|---|---|---|---|---|
| L-carnitine (mg/100 mg) | 20.14 | 19.77 | 20.50 | 19.93 | 20.51 | 20.75 | 20.27 | 1.87% |

Example 14

Detection of Free Carnitine in Plasma

Pretreatment of test plasma: 100 μl plasma (brought from blood-bank), was pipetted and 400 μl of 10% methanol acetonitrile was added in, shaken, oscillated on a vortex mixer for 5 min, centrifuged at 10000 r·min−1 for 10 min, the supernatant was used as sample solution.

Control solution: 35 mg DL-carnitine was weighted precisely and dissolved in 100 mL volumetric flask to volume, then 1 ml solution was pipetted to 100 ml volumetric flask, added water to volume.

The method of example 9 was used for detection and the result was shown in table 13.

TABLE 13

Detection of free carnitine in plasma

| | 1 | 2 | 3 | 4 | 5 | 6 | Average | RSD |
|---|---|---|---|---|---|---|---|---|
| L-carnitine (μmol/L) | 45.12 | 46.32 | 45.85 | 45.77 | 45.91 | 46.52 | 45.92 | 1.06% |

Example 15

Detection of Carnitine Levels in Meat

Meat sample preparation: fresh meat was crushed firstly, 2 g crushed sample was weighted and 25 ml of 10% methanol acetonitrile solution was added, homogenated for 5 min, treated with ultrasound for 30 min, centrifuged at 10000 r·min−1 for 10 min, transferred supernatant, 25 ml of 10% methanol acetonitrile solution was added in the residual, treated with ultrasound for 30 min, centrifuged at 10000 r·min−1 for 10 min, supernatant was combined. It is the sample solution.

100 mg DL-carnitine was weighted precisely and dissolved in 100 mL volumetric flask to volume, then 1 ml solution was pipetted to 100 ml volumetric flask, added water to volume.

The method of example 9 was used for detection and the result was shown in table 14.

TABLE 14

Detection of carnitine leve in Pork, Beef and Lamb

| | 1 | 2 | 3 | 4 | 5 | Average | RSD |
|---|---|---|---|---|---|---|---|
| Pork (g/kg) | 0.22 | 0.22 | 0.23 | 0.24 | 0.24 | 0.23 | 4.35% |
| Beef (g/kg) | 0.64 | 0.68 | 0.66 | 0.65 | 0.62 | 0.65 | 3.44% |
| Lamb (g/kg) | 2.01 | 2.2 | 2.15 | 2.12 | 2.22 | 2.14 | 3.87% |

The invention claimed is:

1. A method for detecting the content of L-carnitine or D-carnitine in a sample comprising L-carnitine or D-carnitine, wherein the method includes following steps:
   (a) preparing a solution comprising the sample containing a proper amount of L-carnitine (or D-carnitine) and a control solution containing DL-carnitine;
   (b) mixing a proper amount of a derivative reagent and the test sample solution containing L-carnitine (or D-carnitine), and allowing them to react to generate L-carnitine (or D-carnitine) derivatives; wherein the derivative reagent has a structure of:

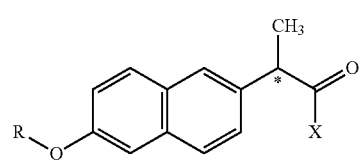

(I)

wherein:
   the carbon atom marked with an asterisk is the chiral carbon atom;
   the compound is chiral compound having pure optical active, the D- or L-compound;

R represents C1-C6 straight-chain or branched alkyl groups, C6-C10 aryl groups, C2-C6 straight-chain or branched alkenyl or alkynyl groups or C3-C6 cycloalkyl groups; and X represents a halogen atom;

(c) subjecting the reacted test sample solution to HPLC to detect and thereafter calculating the content of L-carnitine (or D-carnitine) in the sample.

2. The method according to claim 1, wherein the method further includes following steps:
   (d) preparing the derivatization reagent solution: a D- or L-optical pure compound of formula (I) of claim 1 is dissolved in solvent of claim 6 to form a 0.01~100 mg/ml solution under the dark conditions, wherein the compound of formula (I) is (+)α-methyl-6-methoxy-2-naphthyl acetyl chloride, and the solvent is acetonitrile; the concentration of solution is from 1 to 10 mg/ml;
   (e) preparing a test solution of L-carnitine or D-carnitine, and a control solution of DL-carnitine;
   (f) causing the derivatized reagent of step (d) to mix and react with the test solution and control solution of step (e) respectively in a airtight vessel, in the present of a solvent at 20° C.~95° C. in a water bath for 20-180 min; and
   (g) using high performance liquid chromatography (HPLC) to separate and detect the reacted test solution and control solution, thereafter the content of L-carnitine (or D-carnitine) in test solution is calculated using an external standard method.

3. The method according to claim 1, wherein the sample is selected from pharmaceutical preparations or biological agents, health care products, cosmetics, body fluids and various food products which contain L-carnitine or/and D-carnitine.

4. The method according to claim 1, wherein the sample is a tissue or plasma of a mammal.

5. The method according to claim 1, wherein the sample is selected from various edible plant and animal food articles.

6. The method according to claim 1, wherein the sample is an animal feed.

7. The method according to claim 1, wherein the sample is a supplemental product comprising plant nutrients.

8. The method according to claim 1, wherein in the compound of formula (I), R represents methyl, ethyl, isopropyl, butyl or benzyl, and X represents Cl or Br.

9. The method according to claim 7, wherein the compound of formula (I) is crystalline solid.

10. The method according to claim 9, wherein the compound of formula (I) is selected from (+)α-methyl-6-methoxy-2-naphthyl acetyl chloride, (−)α-methyl-6-methoxy-2-naphthyl acetyl chloride, (+)α-methyl-6-ethoxy-2-naphthyl acetyl chloride and (−)α-methyl-6-ethoxy-2-naphthyl acetyl chloride.

11. The method according to claim 1, wherein optically pure compound of formula (I) and its crystalline solid is dissolved in solvent to form a solution with proper concentration; the solvent is selected from ether, propyl ether, tetrahydrofuran, acetone, methyl ethyl ketone, acetonitrile, propionitrile, ethyl acetate, or the mixture of any two or more solvents above; the concentration is 0.01-100 mg/ml.

12. The method according to claim 11, wherein the solvent is acetonitrile; concentration is 1-10 mg/ml.

13. The method of claim 3, wherein the sample is selected from L-carnitine API, injection, oral solution, tablet, and slimming capsule and drinks.

14. The method of claim 5, where the plant or food article is made from pig, cattle, sheep, chicken, shrimp, fish, eggs, vegetables, fruits and etc.

* * * * *